United States Patent [19]
Osaka et al.

[11] Patent Number: 5,228,972
[45] Date of Patent: Jul. 20, 1993

[54] APPARATUS FOR MEASURING CONCENTRATION OF TEST SUBSTANCE IN LIQUID

[75] Inventors: Tatsuhiko Osaka, Shiga; Koichi Yamasaki, Oumihachiman; Hiroshi Terawaki; Toji Mukai, both of Shiga; Sadaaki Nakaoka, Osaka; Harumi Tanaka; Yoichi Hamada, both of Kobe, all of Japan

[73] Assignee: Daikin Industries, Ltd., Osaka, Japan

[21] Appl. No.: 358,424

[22] Filed: May 30, 1989

[30] Foreign Application Priority Data

May 27, 1988 [JP] Japan .................. 63-131174
Dec. 13, 1988 [JP] Japan .................. 63-314444

[51] Int. Cl.$^5$ .................................. G01N 27/404
[52] U.S. Cl. ...................... 204/415; 204/153.18; 204/400
[58] Field of Search ............ 204/403, 415, 435, 153.18

[56] References Cited

U.S. PATENT DOCUMENTS

| | | | |
|---|---|---|---|
| 3,627,664 | 12/1971 | Grimaldi | 204/400 |
| 3,718,563 | 2/1973 | Krull et al. | 204/415 |
| 3,926,765 | 12/1975 | Haddad | 204/435 |
| 3,997,420 | 12/1976 | Buzza | 204/415 |
| 4,230,537 | 10/1980 | Delente et al. | 204/415 |
| 4,468,271 | 8/1984 | Pierson | 204/419 |
| 4,568,445 | 2/1986 | Cates et al. | 204/419 |
| 4,929,330 | 5/1990 | Osaka et al. | 204/403 |
| 4,933,066 | 6/1990 | Osaka et al. | 204/403 |

FOREIGN PATENT DOCUMENTS 63-243863 10/1988 Japan .

*Primary Examiner*—T. Tung
*Attorney, Agent, or Firm*—Beveridge, DeGrandi, Weilacher & Young

[57] ABSTRACT

A disk-shaped thin plate or a long-sized thin plate having a roll appearance housed in a casing in which openings for penetration of test substance are formed and on which diffusion-limiting membranes are adhered to cover each openings. Also a driving mechanism for moving the thin plate is provided with the casing. The casing thus houses the thin plate and is provided with the driving mechanism and is positioned in a test apparatus body having a concentration measuring electrode therein. Multiple measurments of concentration of a test substance are carried out by moving the thin plate by the driving mechanism to position the diffusion-limiting membrane having the test solution deposited thereon to the position available to contact with the concentration measuring electrode, while keeping the casing placed in the test apparatus body. As a result, a plurality of measurements of concentration of the test substance is carried out easily.

18 Claims, 11 Drawing Sheets

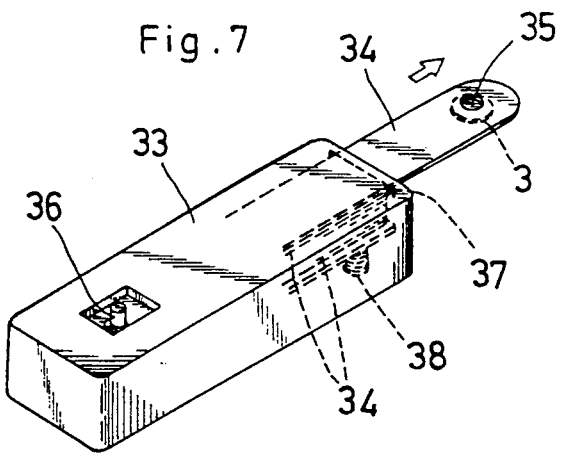
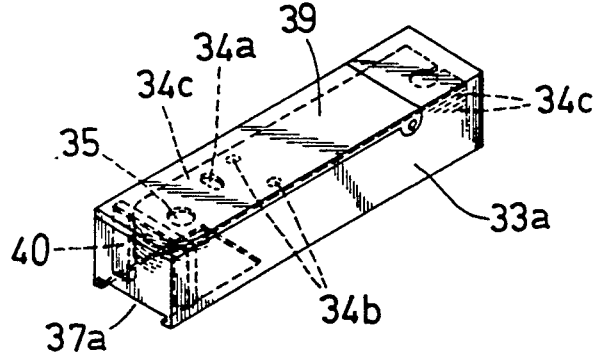
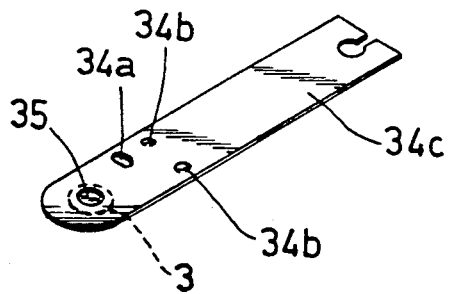
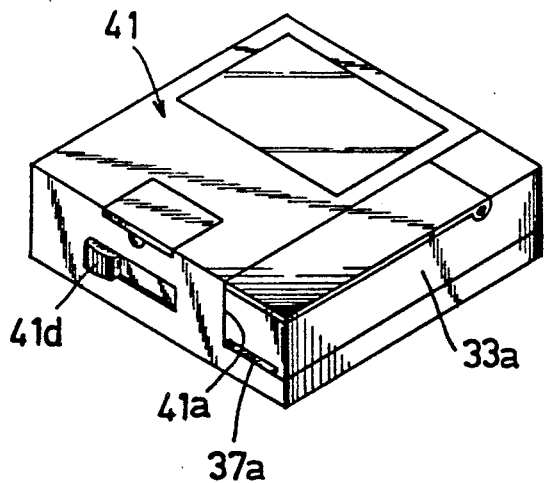

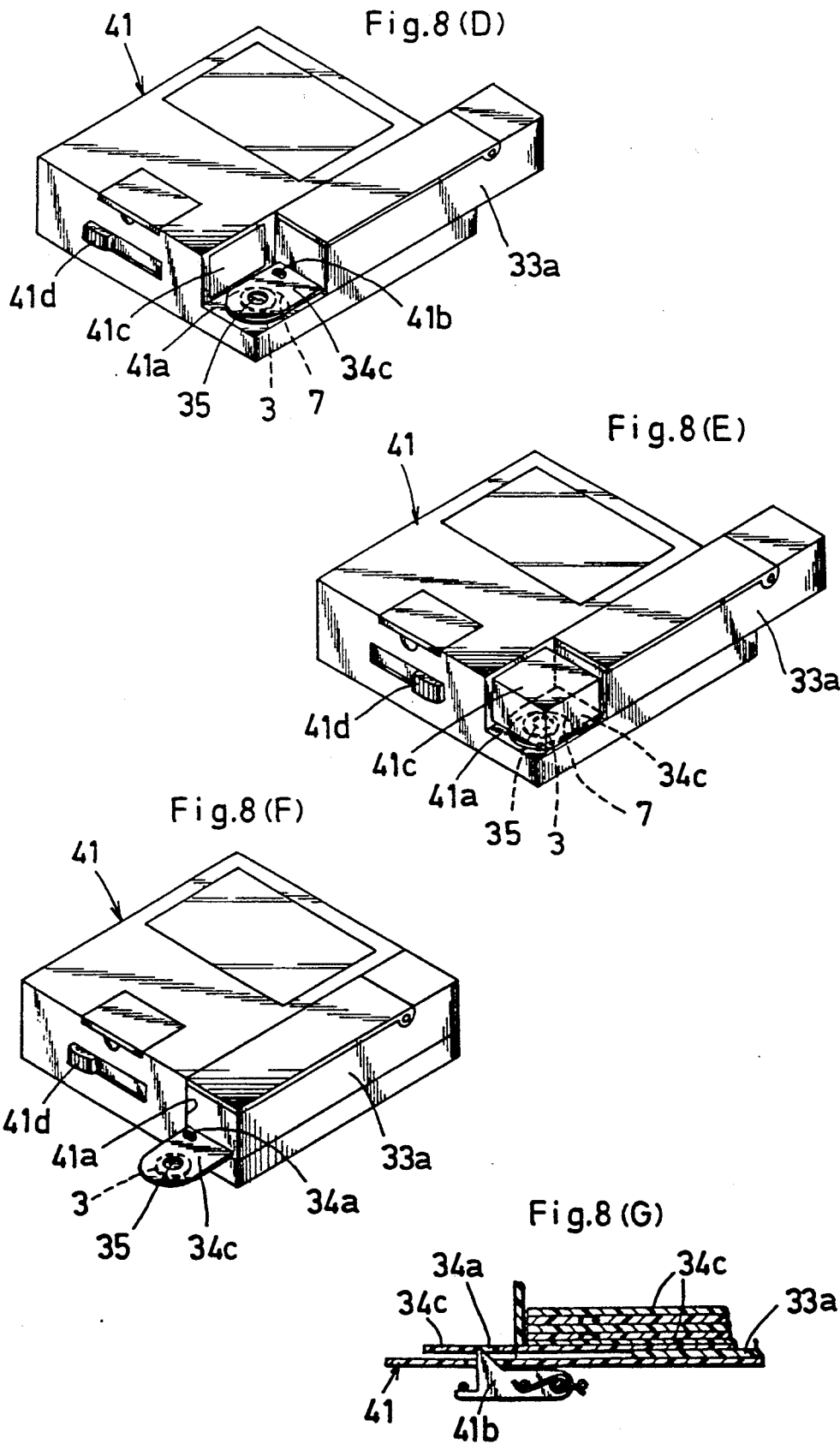

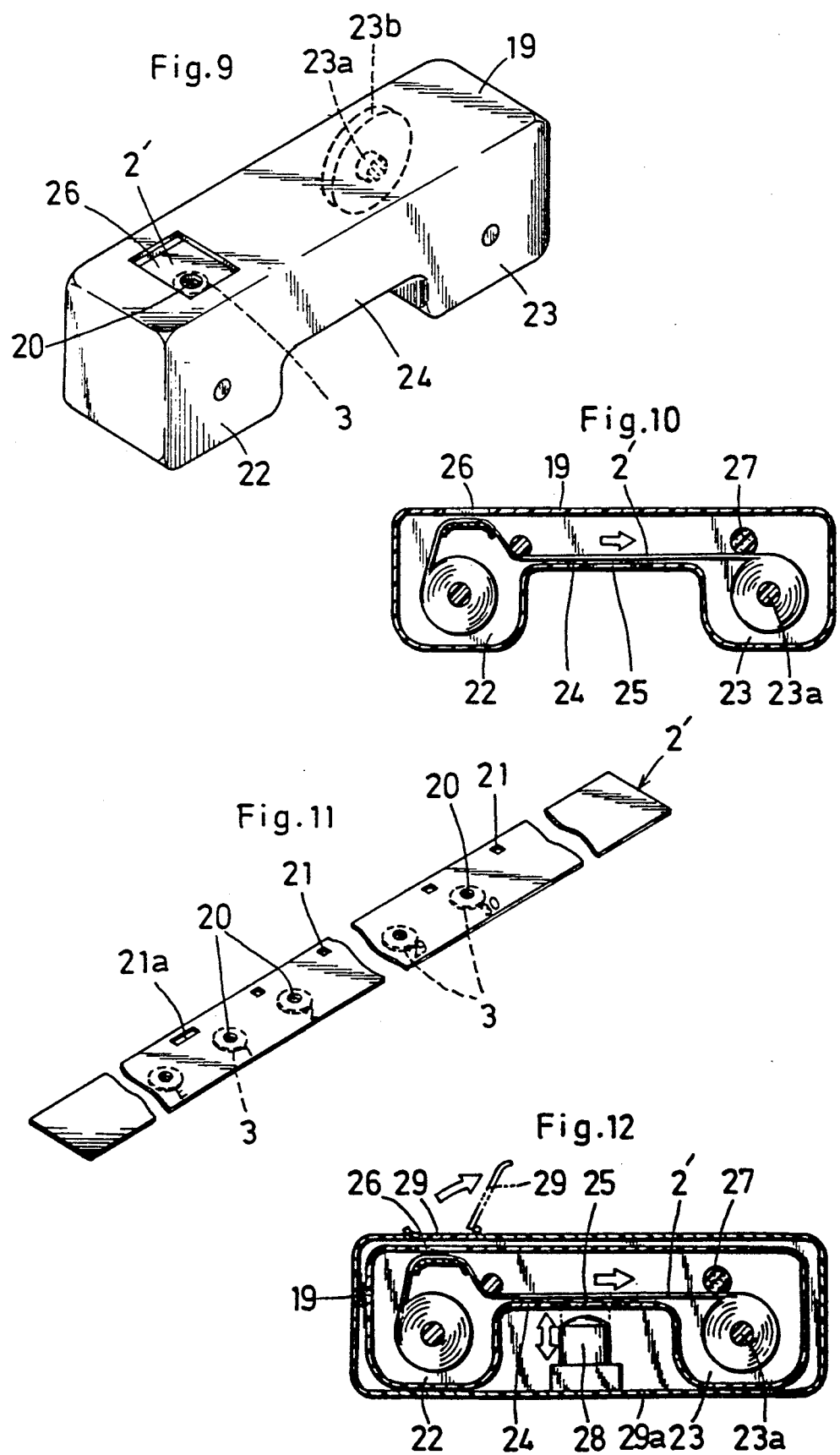

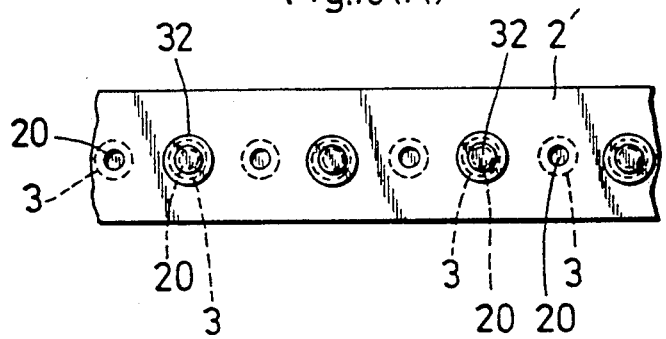
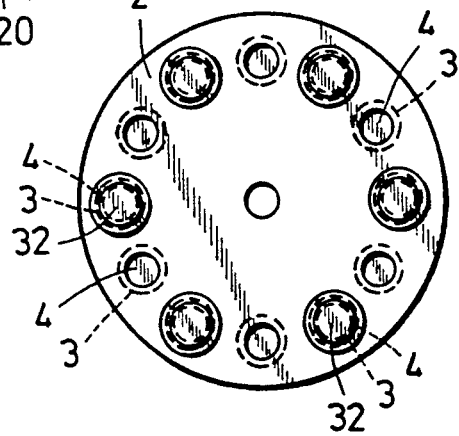
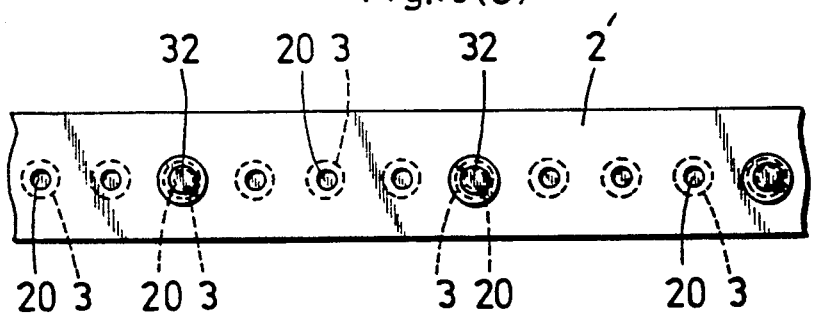
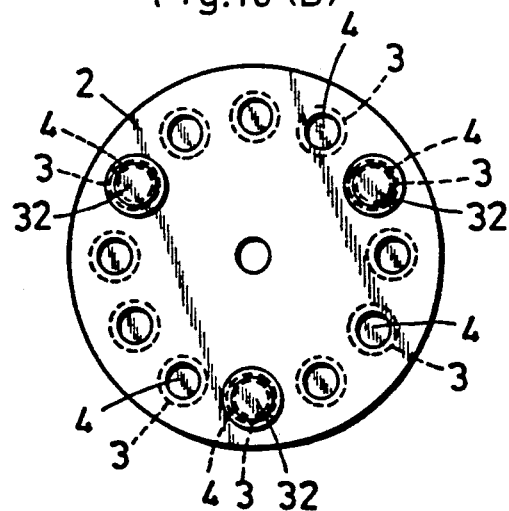

APPARATUS FOR MEASURING CONCENTRATION OF TEST SUBSTANCE IN LIQUID

BACKGROUND OF THE INVENTION

Field of the Invention

This invention relates to an assistant apparatus for measuring concentration of a test substance in liquid suitably used for adhering a diffusion-limiting membrane which is used to increase a concentration measuring limit of a test substance and for simplifying the disposing operation of the diffusion-limiting membrane after the measuring operation. This invention also relates to a concentration measuring apparatus for measuring the test concentration of a substance in liquid, with the assistant apparatus removably instaled thereto. This invention further relates to a method for measuring concentration of a test substance in liquid using the assistant apparatus and the test apparatus.

It is known that a physiologically active substance has a caracteristic capable of selectively detecting a very complicated organic compound, protein or the like with high sensibility. With attention directed to this characteristic, research and development have been made on measurement of such organic compounds, proteins or the like with the use of an enzyme electrode unit having base electrodes on which a physiologically active substance (hereinafter referred to as an enzyme) is immobilized.

When measuring a test substance in a liquid with the use of the enzyme electrode unit above-mentioned, the test substance is oxidized or reduced in the presence of such enzyme. The concentration of the test substance is determined by measuring the amount of a substance produced or consumed in such oxidation or reduction. For instance, when the concentration of glucose is measured using an enzyme electrode consisting of a glucose oxidase as an emzyme and a platinum electrode and a silver electrode as base electrodes, the following reaction occurs.

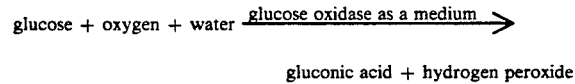

$$\text{glucose} + \text{oxygen} + \text{water} \xrightarrow{\text{glucose oxidase as a medium}} \text{gluconic acid} + \text{hydrogen peroxide}$$

As is apparent from the reaction equation, oxygen is consumed and hydrogen peroxide is produced. So the concentration of glucose is determined by measuring the amount of produced hydrogen peroxide or consumed oxygen.

Accordingly, the upper limit of concentration which can be measured is determined dependent on the amount of a substance provoking such oxidation or reduction, for example the amount of oxygen.

In view of the foregoing, it has been proposed to increase the concentration measuring limit by limiting the penetration rate of a test substance by a diffusion-limiting membrane mounted on the surface of an enzyme-immobilized membrane.

More specifically, there has been adopted an arrangement in which the diffusion-limiting membrane is mounted on a cap to be threadably secured to the base portion of a rod-like enzyme electrode unit, and screwing the cap causes the diffusion-limiting membrane to be automatically contacted with the enzyme-immobilized membrane.

With the use of such an arrangement, the penetration rate of a test substance to be measured is limited by the diffusion-limiting membrane, thereby to achieve measurement of a considerably high concentration. That is, an output signal from the enzyme electrode is lowered by limiting the penetration rate of a test substance, but the output signal is hard to saturate notwithstanding the increase of concentration of a test substance in a liquid. Furthermore the concentration measuring limit is decided by the saturation point. As a result, the concentration measuring limit is increased up to the concentration corresponding to the saturation point. To eliminate the influence of interfering substances contained in a test solution to be measured (for example, increase in diffusion limiting effect resulting from the adhering of such interfering substances), the diffusion-limiting membrane needs to be replaceable. This is the reason for adopting the cap membrane screwing mechanism.(Japanese Patent Laid open No.Sho 63-243863)

When the diffusion-limiting membrane holding means having the arrangement above-mentioned is used, replacement of the diffusion-limiting membrane may be relatively facilitated. There are instances, however, where it becomes very difficult to mount or remove the holding means on or from the base portion of an enzyme electrode unit due to the arrangement of its mounting mechanism, or where it is not possible to achieve a uniform contact of the diffusion-limiting membrane to the enzyme-immobilized membrane due to the degree of the screwing force.

Further, when the enzyme electrode unit base portion has a small diameter, resulting a in decrease in the cap size, this causes the manual mounting/removal operation to be very difficult. This makes the problems above-mentioned more serious.

Moreover, the diffusion-limiting membrane is mounted on a cap, requiring a large space for preserving and/or transporting the same.

Considering above points, it is proposed to employ a diffusion-limiting membrane holder which is constructed with a thin plate having a through hole and a diffusion-limiting membrane adhered to one side of the thin plate to cover the through hole, and measuring the concentration of the test solution under the condition of pressure contacting the diffusion-limiting membrane to the surface of the enzyme electrode unit (refer to U.S. patent application No. 176,288, filed Mar. 31, 1988, now abandoned). Difficulties are encountered in dropping the solution including test substance (hereinafter referred to as test solution) to the through hole through the diffusion-limiting membrane is difficult and pressure contacting the diffusion-limiting membrane to the surface of the enzyme electrode unit. Also, upon completion of the measurement as above-mentioned, a relatively great amount of interfering substances are adhered to the diffusion-limiting membrane. This inevitably degrades the diffusion limiting effect of the diffusion-limiting membrane which is to limit diffusion of a test substance to be measured. Therefore, the diffusion-limiting membrane as it is, cannot assure an accurate measurement on and after the second operation. Accordingly, it is a common practice that, after a predetermined number of measurements have been made, preferably after every measurement has been made, the diffusion-liming membrane is exchanged with new one to achieve measurement without any influence of the interfering substances. As a result, a greater quantity of thin plate than would be needed for contacting the diffusion-limiting membrane must be used. Further, the disposal of used thin plates and the selection of new thin plate is needed. This complicates the series of operations to measure the concentration of the test substance.

More specifically, a series of operations is needed as follows (1) a power switch provided with the concentration measuring apparatus is turned on, (2) a cover provided with the concentration measuring apparatus is opened, (3) a package is opened and a thin plate on which a diffusion-limiting membrane is adhered is picked out, (4) test solution is dropped to the thin plate (if the test solution is blood, blood is drawn, then the blood is deposited to the thin plate), (5) the thin plate is inserted into the concentration measuring apparatus, (6) the diffusion-limiting membrane adhered to the inserted thin plate is pressure contacted to the surface of the electrode for measuring concentration, then the concentration of the test substance is measured, (7) after measurement is made, the diffusion-limiting membrane is released from the surface of the electrode, (8) the thin plate is pulled out from the concentration measuring apparatus, (9) the cover provided with the concentration measuring apparatus is closed,

(10) the pulled out thin plate is disposed of, and

(11) the power switch is turned off.

This series of operations is needed, and particularly time consuming operations are needed, thereby complicating concentration measuring operations as a whole. Further, the above-mentioned series of operations do not include a calibrating operation based on a standard solution having an established concentration of a test substance. In practice the calibrating operation is needed, so the operations are more complicated as a whole.

The description hereinbefore which has discussed mainly the case of concentration measuring of a test substance when using an enzyme electrode unit, may be also applied to the case of concentration measuring of a test substance using another electrode unit, which may also cause the similar problems.

SUMMARY OF THE INVENTION

It is an object of the present invention to simplify the installing and removing operations to and from an electrode and to simplify the disposing operation of a diffusion-limiting membrane, while keeping an increased concentration measuring limit and an improved accuracy of concentration measurement.

In order to achieve the object above-mentioned, the assistant apparatus for measuring concentration of a test substance in a liquid in accordance with the present invention comprises:

one or more thin plates having one or more openings through which a test substance to be measured is penetrated, in a predetermined position thereof, diffusion-limiting membranes for limiting diffusion of the test substance adhered to the thin plates for covering the openings, a casing for housing the one or more thin plates; and a driving mechanism for moving the thin plate by a predetermined distance.

The thin plate may be disk-shaped, strip-shaped or elongated. The elongated thin plate may further be rolled. The disk-shaped or elongated thin plate may further have through holes for passing through the concentration measuring electrode or calibrating standard solution housing member for housing standard solution for calibration. The through holes are formed in the thin plate between adjacent openings. In this case, the openings and through holes may be formed one after the other, or the through holes may be formed in every predetermined number of openings. The calibrating standard solution housing members may be secured to the disk-shaped or elongate thin plate, corresponding to every other openings or every predetermined number of opening. The driving mechanism may be operated manually or may be operated by motor and the like. The driving mechanism may be a mechanism wholly housed in the casing or a mechanism partly housed in the casing. The driving mechanism may also be a mechanism for preventing the movement of the thin plate with the casing in a state that the assistant apparatus is installed in a test apparatus which allows the movement of the casing.

According to the assistant apparatus for measuring concentration of a test substance having the arrangement above mentioned, one or more thin plates on which the diffusion-limiting membranes are adhered, are housed in the casing, thereby to accomplish easy transportation and to contain the diffusion-limiting membranes securely during transportation and taking custody. When the concentration of the test solution is measured, first the one or more thin plates are moved a predetermined distance by the driving mechanism thereby to move one or more openings covered by the diffusion-limiting membrane to a concentration measurement allowed position, secondly the diffusion-limiting membrane is pressure contacted with the surface of the concentration measuring electrode. Then concentration measuring can be carried out under the condition that diffusion of the test substance to the concentration measuring electrode is limited by the diffusion-limiting membrane.

When a proper mechanism suited with the shape and the like of the thin plate is employed as the driving mechanism, then above-mentioned operation can be performed without inconvenience.

In order to achieve the object above-mentioned, the test apparatus for measuring concentration a test substance in accordance with the present invention comprises:

an assistant apparatus having one or more thin plates, a casing, and a driving mechanism for moving the thin plate wherein the one or more thin plates further have one or more openings for enabling penetration of a test substance therethrough and diffusion-limiting membranes for covering each openings adhered to the one or more thin plates, the one or more thin plates are housed in the casing, and the driving mechanism is provided with the casing, a test apparatus body for positioning the assistant apparatus removably therein, and a concentration measuring electrode provided to the test apparatus body.

Preferably, a mechanism for moving the thin plate in a predetermied direction co-operating with the driving mechanism is provided with the test apparatus body.

Also preferably, an electrode driving mechanism for moving the concentration measuring electrode between a position preventing contact with the diffusion-limiting membrane and a position allowing contact with the diffusion-limiting membrane is provided with the test apparatus body.

According to the test apparatus for measuring concentration of a test substance having the arrangement above-mentioned, first the thin plate is moved the predetermined distance by the thin plate driving mechanism under the condition that the assistant apparatus is housed in the test apparatus body, thereby to allow contact of a diffusion limiting membrane with the concentration measuring electrode, secondly the diffusion-limiting membrane is pressure welded with the surface of the concentration measuring electrode, and thirdly a test solution is dropped to the diffusion-limiting membrane. Then concentration measuring with high accuracy can be carried out under the condition that diffusion of the test substance to the concentration measuring elelctrode is limited by the diffusion-limiting membrane. When a concentration measuring operation is not carried out or when the concentration measuring operation is finished, the assistant apparatus can easily be disposed, exchanged or safeguarded and so on by removing the assistant apparatus from the test apparatus body.

In order to achieve the object above-mentioned, the method for measuring concentration of a test substance in a liquid in accordance with the present invention, using an assistant apparatus having one or more thin plates which have one or more openings each covered with a diffusion-limiting membrane, a casing for housing the thin plates therein and a driving mechanism for moving the thin plate, and a test apparatus having a test apparatus body and a concentration measuring electrode for outputting an electric signal corresponding to a concentration of a test substance, comprising steps of:

depositing a liquid on the diffusion-limiting membrane;

positioning the assistant apparatus in the test apparatus body;

moving the thin plate by a predetermined distance for positioning the opening opposite to the concentration measuring electrode;

pressure contacting the concentration measuring electrode with the diffusion-limiting membrane.

measuring concentration of the test substance in the liquid based on the electric signal;

detaching the concentration measuring electrode from the diffusion limiting membrane.

The thin plate may be disk-shaped and the moving step may be automatically carried out following the step of positioning the assistant apparatus in the test apparatus body. The thin plate also may be elongated. The deposition step may be carried out after the positioning step, and the moving step may be carried out before or after the depositing step. Furthermore, the depositing, moving pressure contacting, measuring and detaching steps may be repeated a predetermined number of times.

The above, and other objects, features and advantages of this invention will be apparent from the following detailed description of illustrative embodiments which is to be read in connection with the accompanying drawings.

BRIEF DESCRIPTION OF THE DRAWINGS

FIG. 7 is a schematic perspective view of an assistant apparatus in accordance with a fourth embodiment of the present invention;

FIG. 8A is a schematic perspective view of an assistant apparatus in accordance with a fifth embodiment of the present invention;

FIG. 8B is a perspective view showing a thin plate in FIG. 8A;

FIG. 8C is a schematic perspective view of a test apparatus in which the assistant apparatus in FIG. 8A is installed;

FIGS. 8D to 8F are perspective views showing measuring operations of the test apparatus in FIG. 8C;

FIG. 8G is a vertical section view of the main portion of the test apparatus in FIG. 8C;

FIG. 9 is a schematic perspective view of an assistant apparatus in accordance with a sixth embodiment of the present invention, FIG. 10 is a vertical section view of the center portion of the assistant apparatus in FIG. 9:

FIG. 11 is a partial cutaway perspective view of an elongated film housed in the assistant apparatus in FIG. 9;

FIG. 12 is a simplified vertical section view of the center portion of a test apparatus in which the assistant apparatus in FIG. 9 is installed;

FIGS. 16A and 16C are plan views of a further modified elongated film respectively;

FIGS. 16B snd 16D are plan views of a further modified disk shaped thin plate respectively;

DESCRIPTION OF THE PREFERRED EMBODIMENTS

Figure 1:
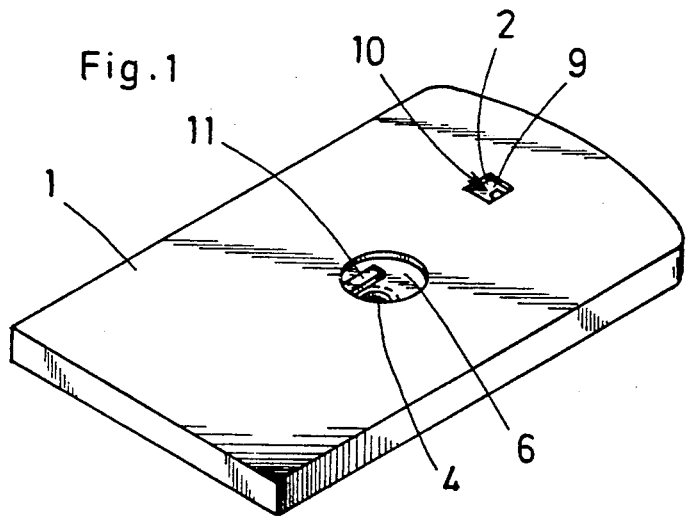
FIG. 1 is a perspective view of an assistant apparatus for measuring concentration of a test substance in accordance with a first embodiment of the present invention.
Figure 2:
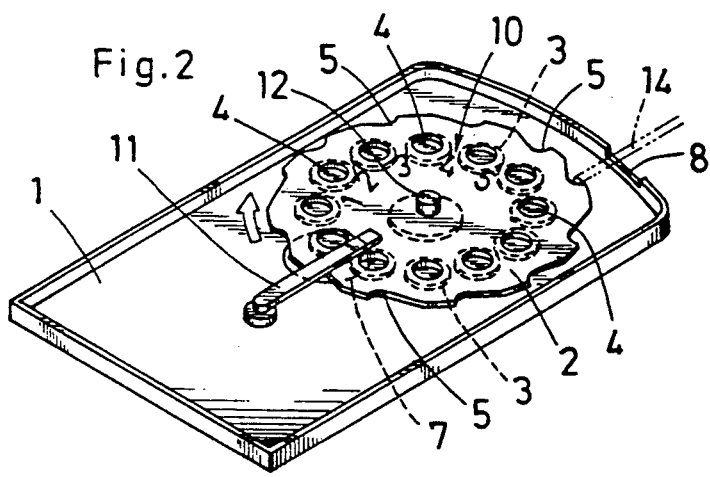
FIG. 2 is a perspective view showing an inner mechanism of the assistant apparatus in FIG. 1.
Figure 3:
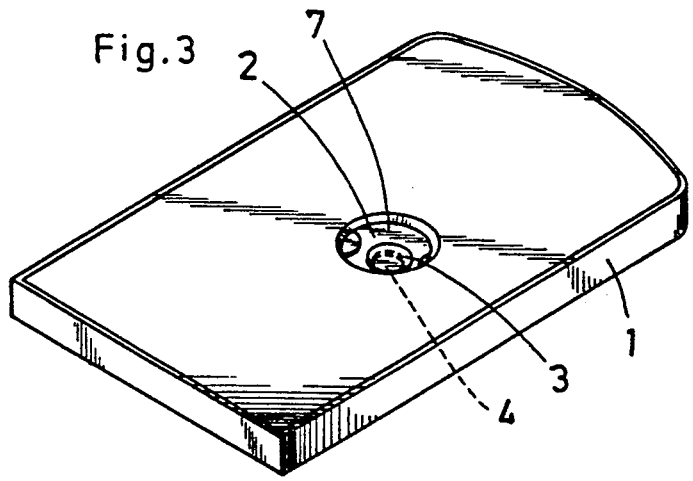
FIG. 3 is a rear perspective view of the assistant apparatus in FIG. 1.

FIG. 1 is a perspective view of an assistant apparatus in accordance with a first embodiment of the present invention. FIG. 2 is a perspective view thereof showing an inner mechanism. FIG. 3 is a rear perspective view thereof.

In FIGS. 1, 2 and 3, a disk-shaped thin plate 2 is rotatably housed in a thin casing 1, and a plural number of diffusion-limiting membranes 3 are adhered to the disk-shaped thin plate 2. The disk shaped thin plate 2 has tolerance against a test solution. At the peripheral portion of the disk-shaped thin plate 2, a plural number of holes 4 allowing penetration of a test substance, are formed ar regular intervals. At the edge portion of the disk-shaped thin plate 2, a plural number of notches 5 for rotating are formed at the same intervals as the holes 4. Diffusion-limiting membranes 3 are adhered to one side of the disk-shaped thin plate 2 to cover each hole 4. The diffusion-limiting membrane 3 separates interfering particles like blood corpuscles and the like from test solution as its main function, and may consist of a polycarbonate membrane having a plurality of minute pores. As a result, when a diffusion limiting membrane for limiting penetration of the test substance is secured to a concentration measuring electrode 15, which will be described later, the diffusion-limiting membrane 3 prevents the diffusion-limiting membrane secured to the concentration measuring electrode 15 from being clogged. The diffusion-limiting membrane 3 may consist of the membrane to limit penetration of the test substance, and the diffusion-limiting membrane secured to the concentration measuring electrode 15 may be omitted. The diffusion-limiting membrane 3 is employed for separating interfering particles from the test substance as its main function. In this case the diffusion limiting membrane 3 is adhered to the disk shaped thin plate 2. It is preferable that the diffusion-limiting membrane be secured to the surface of the concentration measuring electrode 15. This prevents the accuracy of measurement from being lowered due to the interfering particles.

The casing 1 has enough inner space to prevent test solution dropped to the predetermined position of the disk-shaped thin plate 2 from staining the casing 1, and has a support shaft 12 for supporting the disk-shaped thin plate 2 rotatably therein. An opening 6 for dropping test solution is formed at the predetermined position opposite to one of the holes 4 of the disk-shaped thin plate 2 on the front side of the casing 1. Also, a through hole 7 for allowing insertion of a concentration measuring electrode 15 is formed in the predetermined position opposite to the shifted position at a unit rotating angle from the hole 4 of the rear side of the casing 1. Further, a through hole 8 parallel to the disk-shaped thin plate 2 is formed at the predetermined position of the casing 1, thereby to engage a driving rod 14 coming into the casing 1 through the through hole 8 with one of the notches 5 whereby the disk-shaped thin plate 2 is rotated a predetermined unit angle, by installing the casing 1 on a test apparatus body 13. Furthermore, a window 9 for recognizing any quantity indications 10 displayed at the predetermined position of the disk-shaped thin plate 2, is formed in the predetermined position on the front side of the casing 1. Moreover, a wiping member 11 for wiping excess test solution is secured to the inner predetermined position downstream side from the dropping position of the test solution, in the casing 1.

Figure 4:
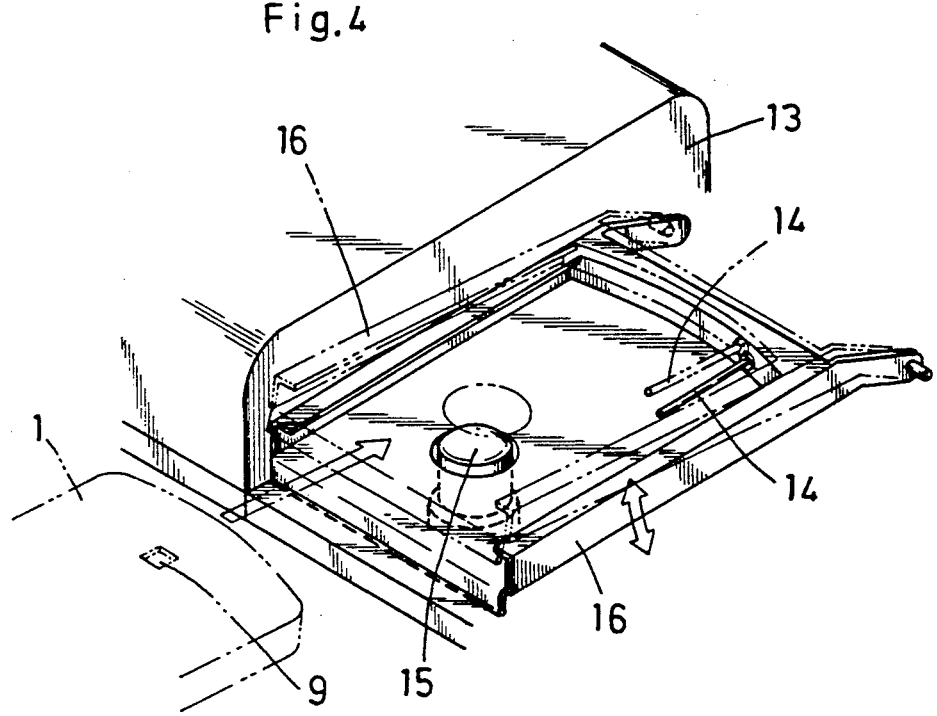
FIG. 4 is a schematic perspective view showing a main portion of a test apparatus in which the assistant apparatus in FIG. 1 can be removably installed.

FIG. 4 is a schematic perspective view showing a main portion of a test apparatus to which the assistant apparatus is removably installed.

The concentration measuring electrode 15 is secured to the predetermined position of the test apparatus body 13. An installing guiding member 16 for guiding the installation of the casing 1 therein is provided rotatably up and downward direction, with the predetermined position of the test apparatus body 13. The driving rod 14 for rotating the disk-shaped thin plate 2 is secured to the innermost position of the installing guiding member 16. Further, a locking mechanism (not shown) for keeping the installing guiding member 16 at the upward rotated position or the downward rotated position selectively, is secured to the inner predetermined position of the test apparatus body 13. Various measuring electrodes may be used as the concentration measuring electrode 15 corresponding to the species of test substance. For example, a concentration measuring electrode having an arrangement that at least a glucose oxidase immobilized membrane is secured to a foundation electrode consisting of platinum and silver, is preferably used for measuring the concentration of glucose.

Methods for measuring blood sugar using the assistant apparatus and the test apparatus both having the arrangement above-mentioned, are described hereinafter.

After blood is deposited onto the diffusion-limiting membrane 3 through the opening 6 formed in the casing 1, the casing 1 is positioned in the installing guiding member 16. Then the installing guiding member 16 is rotated downward. Subsequently, measuring operations for blood sugar are carried out as follows. When placing the casing 1 in the installing guiding member 16, the top edge portion of the driving rod 14 is received in the casing 1 through the through hole 8, and is engaged with the corresponding notch 5, thereby to rotate the disk-shaped thin plate 2 by a unit rotating angle around the support shaft 12 as the rotary axis. A unit rotating angle of the disk-shaped thin plate 2 is previously set in correspondence with the interval of the holes 4 for allowing penetration of the test substance, so that the disk-shaped thin plate 2 is rotated automatically by the driving rod 14, and the excess blood on the disk shaped thin plate 2 is wiped away by the wiping member 11, and finally, the opening 4 positions opposite to the through hole 7 for allowing insertion of a concentration measuring electrode 15. After that, the diffusion-limiting membrane 3, having the blood thereon, is pressure contacted to the surface of the concentration measuring electrode 15 by downwardly rotating the installing guiding member 16 with the casing therein, then blood sugar can be measured under the condition that the concentration of glucose is depressed as a result of the limited diffusion of glucose. After the measurement of blood sugar is finished, the casing 1 is departed from the concentration measuring electrode 15 by moving the installing guiding member 16 upwardly, then the casing 1 can easily be removed from the installing guiding member 16. Accordingly, with the casing 1 removed, the next diffusion-limiting membrane 3 moves opposite to the opening 6. So, measurement of blood sugar can be repeated by again performing the series of operations above-mentioned. Finally if all the diffusion-limiting membranes 3 in the casing 1 are used for measurement of blood sugar, only the the disk shaped thin plate 2 need be disposed of or the casing 1 housing the disk-shaped thin plate 2 therein need be disposed of. From the viewpoint of simplifying the disposal operation and preventing of infection resulting from disease germs and the like, the latter disposal operation is preferably employed.

As is apparent from the foregoing, operability for positioning and removing the disk-shaped thin plate 2 are improved in comparison with the operability for positioning and removing only the disk-shaped thin plate 2, in spite of the very thin thickness of the disk-shaped thin plate 2 and the diffusion-limiting membrane 3. The reason is that the positioning and removing operation is achieved by picking the casing 1 to have enough physical strength and the like. Further, the quantity indication 10 can be recognized from the outer side of the casing 1 through the window 9, thereby preventing the diffusion-limiting membrane 3 from being used twice for measuring blood sugar. Excess blood on the disk-shaped thin plate 2 is wiped away by the wiping member 11, thereby preventing the excess blood on the disk-shaped thin plate 2 from drying, resulting in the disk-shaped thin plate 2 and diffusion-limiting membrane 3 becoming stained by the pulverulent bodies. Further the wiping member 11 may include an antiseptic solution, thereby preventing the blood wiped away from the disk-shaped thin plate 2 from becoming contaminated. The opening 6 for depositing the blood to the disk shaped thin plate 2 is not opposite the through hole 7 for allowing insertion of the concentration measuring electrode 15, thereby to prevent touching a finger and the like with the concentration measuring electrode 15 interposing the diffusion-limiting membrane 3. As a result, the possibility of infection resulting from disease germs and the like remaining on the concentration measuring electrode 15 is prevented from occurring without adopting special mechanisms for preventing infection.

In the embodiment above-mentioned, the concentration measuring electrode 15 is not secured with a diffusion-limiting membrane at its top surface, and the desired diffusion limiting effect is performed only by the diffusion-limiting membrane 3 adhered to the disk-shaped thin plate 2. Preferably the concentration measuring electrode 15 has secured to it a diffusion-limiting membrane performing a high diffusion limiting effect for the test substance at its top surface, and the diffusion-limiting membrane 3 performing a relatively lower diffusion limiting effect for the test substance and performing a high penetration preventing effect for an interfering particle having a large diameter like a blood corpuscle, thereby to supress greatly the variation of the diffusion limiting effect as a whole and to perform precise measurement of blood sugar by securely preventing the penetration of the interfering particles. This series of operations is described in detail in U.S. patent application No. 176,287, filed Mar. 31, 1988, now abandoned.

Further the casing 1 can easily move downward because of its relatively high physical strength. The concentration measuring electrode 15 is contacted with or apart from the diffusion-limiting membrane 3 selectively, following the movement of the casing 1.

The diffusion-limiting membrane 3 adhered to the disk-shaped thin plate 2 to cover a plural number of openings 4 may be a large membrane having the same shape as the disk-shaped thin plate 2. In this case, the large membrane does not act as one diffusion-limiting membrane as a whole, but acts as a plural number of diffusion-limiting membranes only at the portion opposite to each opening 4. This arrangement is equivalent with the arrangement wherein a plural number of diffusion-limiting membranes 3 are housed in the casing 1.

Second Embodiment

Figure 5:
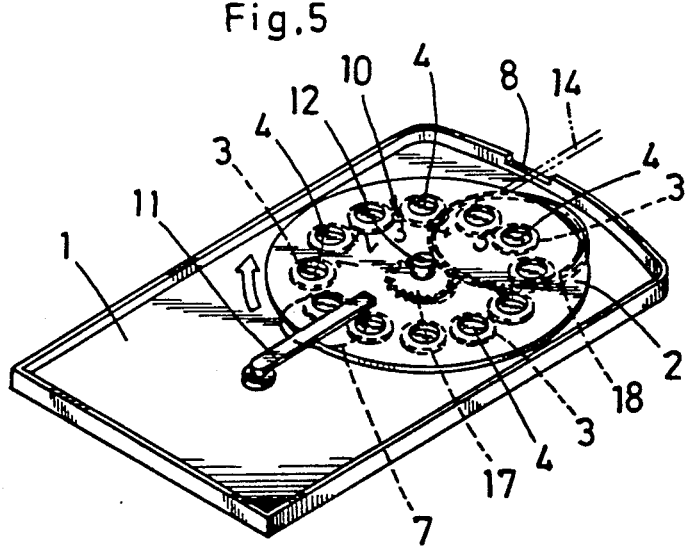
FIG. 5 is a schematic perspective view showing a main portion of an assistant apparatus in accordance with a second embodiment of the present invention.

FIG. 5 is a schematic perspective view showing the main portion of an assistant apparatus in accordance with a second embodiment of the present invention.

Different points from the first embodiment are as follows:

(1) A toothed wheel 17 is provided at the center of the disk-shaped thin plate 2 as one body, and (2) a toothed wheel 18 is provided at the predetermined position of the casing 1, for being rotated by a predetermined angle by the driving rod 14 and for rotating the toothed wheel 17 by an angle corresponding to the interval of the openings 4.

In this embodiment, the toothed wheel 18 is rotated by a predetermined angle by the driving rod 14, after placing the casing 1 in the installing guiding member 16, then the disk-shaped thin plate 2 together with the toothed wheel 17 is rotated by a predetermined angle, thereby to move the diffusion-limiting membrane 3 having deposited blood through the opening 6 to the position opposite to the through hole 7 for allowing for insertion of the concentration measuring electrode 15.

As a result, the measurement of blood sugar can be performed repeatedly, only by carrying out the same manual operations as in the first embodiment.

In this embodiment the toothed wheel 17 is provided at the center of the disk-shaped thin plate 2 in one body, teeth for engaging with the toothed wheel 18 may be formed at the edge outer surface of the disk-shaped thin plate 2, instead of the toothed wheel 17, if the disk-shaped thin plate 2 has the thickness at some degree. Then a similar function as in the first embodiment can be performed.

Further in both embodiments the disk-shaped thin plate 2 is automatically rotated following the placing operation of the casing 1. But the disk-shaped thin plate 2 may be rotated by a manual operation.

Third Embodiment

Figure 6A:
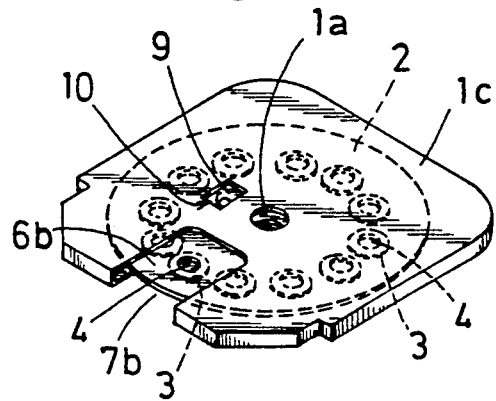
FIG. 6A is a schematic perspective view of an assistant apparatus in accordance with a third embodiment of the present invention.

FIG. 6A is a schematic perspective view of an assistant apparatus in accordance with a third embodiment of the present invention.

Different points from the second embodiment are as follows:

(1) An opening 6b and a through hole 7b opposite to each other are formed by cutting away a predetermined edge portion of a casing 1C.

(2) Holes 1a for allowing insertion of a shaft 1b for rotating a disk-shaped thin plate 2, are formed in the center of the casing 1c.

(3) Toothed wheels 17 and 18 are omitted, also notches 5 are omitted.

Figure 6B:
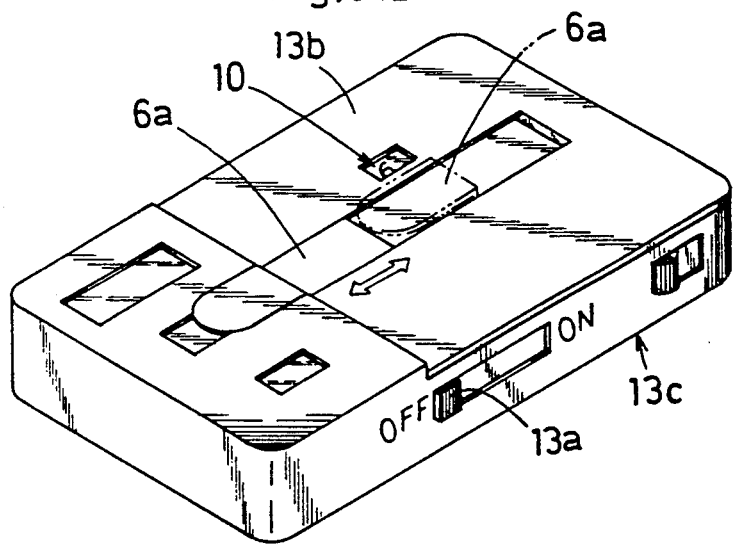
FIG. 6B is a perspective view of a test apparatus in which the assistant apparatus in FIG. 6A is installed.
Figure 6C:
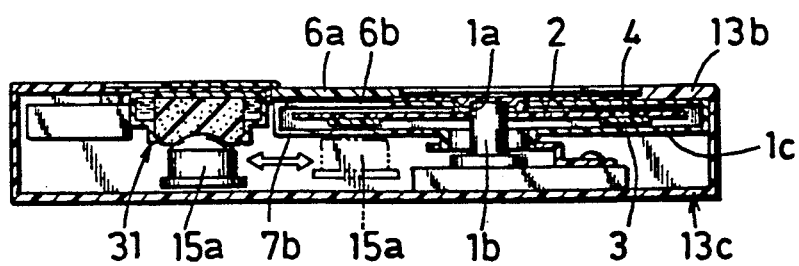
FIG. 6C is a vertical section view of the center portion of the test apparatus in FIG. 6B.

FIG. 6B is a perspective view showing a test apparatus in which the assistant apparatus is installed, while FIG. 6C is a vertical section view at the center portion in FIG. 6B. The test apparatus is used for a plural number of concentration measurement of a test substance.

A main cover 13b is provided in an openable and closable manner for allowing positioning and removing of the casing 1c, within the top predetermined position of a test apparatus body 13c. A small cover 6a is provided slidably to cover the opening 6b, at a predetermined position of the main cover 13b. A wetting liquid housing member 31 is secured in the predetermined position of the test apparatus body 13c. The shaft 1b is provided rotatably at the predetermined position of the test apparatus body 13c. A driving source (not shown) for rotating the shaft 1b is secured in the predetermined position of the test apparatus body 13c. A concentration measuring electrode 15a is provided in the test apparatus body 13c. The concentration measuring electrode 15a is movable between positions opposite to the through hole 7b and the wetting liquid housing member 31. A controlling section (not shown) including a motor and others is provided with the test apparatus body 13c, for opening the small cover 6a and moving the concentration measuring electrode 15a toward the through hole 7b when a switch 13a is turned on, for rotating the shaft 1b causing the disk-shaped thin plate 2 to rotate by a predetermined angle, and for closing the small cover 6a and moving the concentration measuring electrode 15a toward the wetting liquid housing member 31, when the switch 13a is turned off.

In this embodiment a plural number of concentration measurements of a test substance are allowed to be carried out by opening the main cover 13b and positioning the assistant apparatus housing the disk-shaped thin plate 2 therein in the test apparatus body 13c. After that, the switch 13a is turned on thereby permitting the small cover 6a to be opened and to allow the test solution to be deposited to the opening 4 of the disk-shaped thin plate 2. Also the concentration measuring electrode 15a is moved toward the through hole 7b and finally is pressure contacted with the diffusion-limiting membrane 3. Detection of the concentration of the test substance is performed based on the output signal from the concentration measuring electrode 15a. After the concentration of the test substance has detected, the switch 13a is turned off thereby closing the small cover 6a moving the concentration measuring electrode 15a toward the wetting liquid housing member 31, and rotating the disk-shaped thin plate 2 by the shaft 1b. As a result, preparation for next concentration measurement of the test substance is finished.

According to the embodiment above mentioned, the assistant apparatus is allowed to be kept positioned in the test apparatus body 13c. As a result, there is no necessity for carrying the placing and removing operations of the assistant apparatus per every concentration measurement, the operability of the concentration measuring operations is improved.

Fourth Embodiment

FIG. 7 is a schematic perspective view of an assistant apparatus in accordance with a fourth embodiment of the present invention.

A plural number of strip shaped thin plates 34 are housed in a piled up manner, in a casing 33 having a predetermined shape. An opening 35 for penetration of the test substance is formed in a predetermined position of the thin plate 34. A diffusion-limiting membrane 3 is adhered to the thin plate 34 to cover the opening 35. A lever 36 for sending out the uppermost thin plate 34, is provided at the predetermined position of the casing 33 and adopted to move in and out. A spring 38 for energizing thin plates 34 upwardly is provided in the casing 33. An opening 37 for allowing the uppermost thin plate 34 to be sent out is formed at the position opposite to the uppermost thin plate 34, of the casing 33.

In this embodiment firstly, the uppermost thin plate 34 is sent out from the casing 33 through the opening 37 by operating the lever 36. Secondly, blood is deposited into the opening 35 of the thin plate 33. Thirdly, the thin plate 34 together with the casing 33 is placed in a test apparatus body (not shown). Finally, the measurement of blood sugar is carried out. After measurement of blood sugar has finished, the assistant apparatus is removed from the test apparatus body. Secondly, the thin plate 34 is extracted from the casing 33 and is disposed manually. Then measurements of blood sugar can be repeated by carrying out the series of operations mentioned above.

In this embodiment, the thin plate 34 together with the casing 33 is installed in the test apparatus body, but the thin plate 34 may be extracted from the casing 33, and only the extracted thin plate 34 may be installed in the test apparatus body.

Fifth Embodiment

FIG. 8A is a schematic perspective view of an assistant apparatus in accordance with a fifth embodiment of the present invention, while FIG. 8B is a perspective view of a thin plate housed in the assistant apparatus.

Different points from the fourth embodiment are as follows:

(1) An openable cover 39 for resupplying thin plates 34c is provided with the top of a casing 33a.

(2) At least the front edge portion of the bottom face of the casing 33a is opened.

(3) An opening 37a is formed at the bottom edge of the front plate of the casing 33a.

(4) A pair of engaging members 40 for driving the thin plate 34c are secured at the predetermined position of the casing 33a.

(5) An engaging hole 34a engagable with one of a pair of stopping members 41b (see FIG. 8G) for preventing a sliding movement of the thin plate 34c described later), is formed at an edgeward predetermined position of the thin plate 34c.

(6) Upward projections 34b engagable with the engaging members 40, are formed in the predetermined position of the thin plate 34c.

FIG. 8C is a perspective view of a test apparatus body to the assistant apparatus, while FIGS. 8D to 8G show the apparatus during concentration measuring operations.

The assistant apparatus in FIG. 8A is installed at a step portion 41a formed in a predetermined position of the test apparatus body 41. The assistant apparatus is positioned in the test apparatus body by sliding it to and from a predetermined position for a predetermined distance. As shown in FIG. 8G, a pair of stopping members are provided at predetermined positions on the apparatus body 41 to prevent sliding movement of the thin plate 34c in spite of sliding of the casing 33a in the predetermined direction (in FIG. 8G, righthand direction). A pressing member 41c being adopted for sliding movement into the step portion 41a when the casing 33a is moved in the righthand direction, is provided at the predetermined position of the test apparatus body 41. A control section (not shown), including a motor and others for moving the pressing member 41c and a concentration measuring electrode (not shown) into connection with tho pressing member 41c when a switch 41d is operated, is provided at the predetermined position of the test apparatus body 41.

In this embodiment, the opening 35 for allowing penetration of the test substance of the lowermost thin plate 34c is revealed by sliding the casing 33a in a righthand direction (see FIG. 8D), then depositing the test solution into the opening 35 is allowed. Secondly, the pressing member 41c and the concentration measuring electrode are moved by operating the switch 41d, to pressure contact the diffusion-limiting membrane 3 with the surface of the concentration measuring electrode (see FIG. 8E), then concentration measuring is carried out. Thirdly, the casing 33a is returned after the pressing member 41c and the concentration measuring electrode have returned. The lowermost thin plate 34c is sent out from the test apparatus body 41 following the returning movement of the casing 33a, by engaging the engaging members 40 with the upward projections 34b. Finally, the used thin plate 34c is projected from the test apparatus body 41 (see FIG. 8F), then the thin plate 34c is easily extracted and disposed manually.

Sixth Embodiment

FIG. 9 is a schematic perspective view of an assistant apparatus in accordance with a sixth embodiment of the present invention, while FIG. 10 is a vertical section view of the center portion thereof.

The different points of the apparatus of this embodiment from the foregoing embodiments are as follows:

(1) A plural number of diffusion-limiting membranes 3 are adhered to an elongated film 2'.

(2) The elongated film 2' is housed in one end of a casing 19 in a rolled state.

(3) The rolled elongated film 2' is moved toward the other end of the casing 19 by a predetermined distance.

The elongated film 2' has tolerance against the test solution and has openings 20 for allowing penetration of the test substance at an interval of predetermined distance (see FIG. 11). Diffusion-limiting membranes 3 are adhered to the elongated film 2' to cover each opening 20 (see FIG. 11). Holes 21 for detecting the position of the opening 20 are formed at the edge portion of the elongate film 2', and the holes 21 are positioned at predetermined locations relative to the openings 20 (see FIG. 11). An elongated hole 21a is formed at the edge portion of the elongated film 2' in connection with the last opening 20 (see FIG. 1).

The casing 19 has a supplying chamber 22 for housing the elongated film 2' in a rolled manner, a receiving chamber 23 for rolling the received elongated film 2' and a bridging member 24 connecting the supplying chamber 22 and the receiving chamber 23. A through hole 25 for allowing insertion of a concentration measuring electrode is formed in the predetermined position of the bottom plate of the bridging member 24. An opening 26 for allowing deposition of the test solution to the elongated film 2' is formed in the predetermined position of the top plate of the bridging member 24. A wiping member 27 is secured to the receiving chamber 23. A rotary shaft 23a provided with the receiving chamber 23 is projected therefrom. A rotary engaging mechanism 23b, for engaging with a driving system (not shown) provided with a test apparatus, is provided with the projecting portion of the rotary shaft 23a.

FIG. 12 is a simplified vertical section view of a test apparatus body in which the assistant apparatus in FIGS. 9 and 10 is installed.

A concentration measuring electrode 28 is provided with a test apparatus body 29a at the opposite position to the through hole 25, wherein the concentration measuring electrode 28 is movable in an up and down manner. An openable cover 29 is provided on the test apparatus body 29a at the opposite position to the opening 26.

A moving mechanism (not shown) operating automatically or operated by closing a cover 29 after the deposition operation has completed, is provided at the predetermined position of the test apparatus body 29a. The moving mechanism operates to move the elongated thin film 2' to the receiving chamber 23. An elevating mechanism (not shown) is provided at the predetermined position of the test apparatus body 29a. The elevating mechanism operates to elevate a concentration measuring electrode 28 provided with the test apparatus body 29a, to contact with the diffusion-limiting membrane 3. The moving mechanism and elevating mechanism can easily be constructed using a motor, toothed wheels, ball screws and others, and a timing controlling apparatus consisting of a microcomputer and the like.

The concentration measuring operations of blood sugar using the test apparatus with the assistant apparatus installed therein, are as follows.

Initially, blood is deposited onto the corresponding diffusion-limiting membrane 3 through the opening 26 by opening the cover 29 of the test apparatus body 29a. Secondly, the elongated film 2' is moved a predetermined distance by the moving mechanism, to opposite the diffusion-limiting membrane 3 with the blood deposited thereon with the concentration measuring electrode 28. Thirdly, the concentration measuring electrode 28 is elevated by the elevating mechanism, thereby to pressure contact the concentration measuring electrode 28 with the diffusion-limiting membrane 3. Then the concentration measurement covering a wide range can be carried out with high accuracy based on the concentration of glucose limited by the penetration thereof. The blood remaining at the diffusion-limiting membrane 3, with which measurement is already carried out, is wiped away by contacting the diffusion-limiting membrane 3 with the wiping member 27 during the moving period of the elongated film 2'.

As is apparent from the foregoing, the concentration measuring position is apart from the blood depositing position, thereby to prevent contamination without any special contamination preventing mechanism. The casing 19 can be kept positioned in the test apparatus body 29a up to the point where all of the diffusion-limiting membranes 3 for measuring blood sugar are used up. This simplifies the necessary operations for measuring blood sugar. The number of tests for measuring blood sugar can easily be increased by increasing the number of the diffusion-limiting membranes 3 adhered to the elongate film 2', because the rolled elongated film 2' can easily be lengthened simply by making the supplying chamber 22 and receiving chamber deeper, in comparison with the disk-shaped thin plate being adhered to the diffusion-limiting membranes thereto.

Seventh Embodiment

Figure 13A:
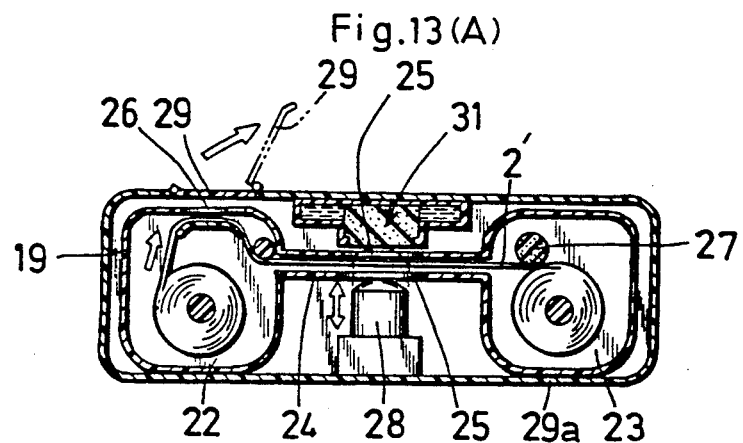
FIG. 13A is a simplified vertical section view of the center portion of a test apparatus in which an assistant apparatus in accordance with seventh embodiment of the present invention is installed.
Figure 13B:
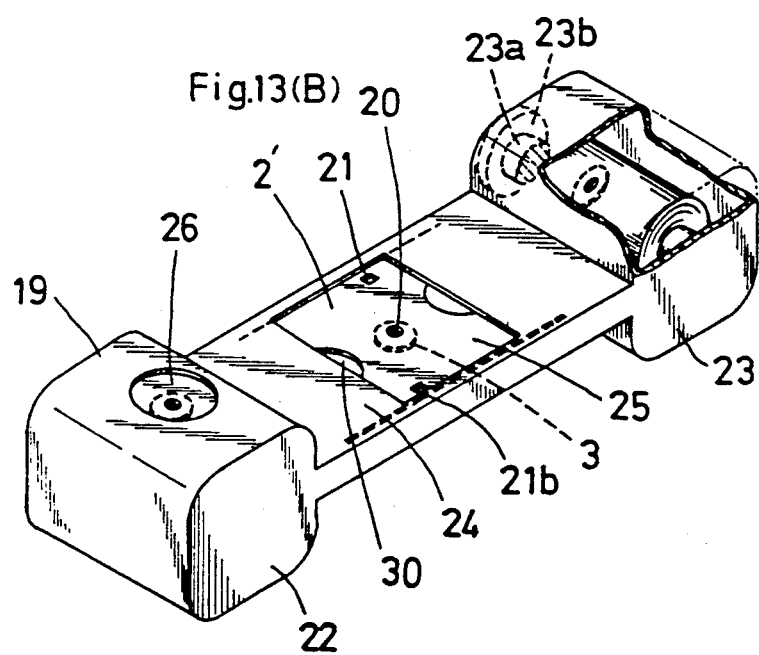
FIG. 13B is a partial cutaway perspective view of the assistant apparatus in FIG. 13A.
Figure 13C:
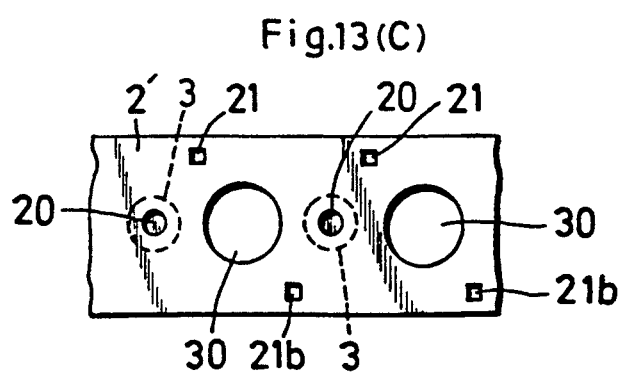
FIG. 13C is a partial plan view of an elongated film housed in the assistant apparatus in FIG. 13B.

FIG. 13A is a simplified vertical section view at the center portion of a test apparatus body in which an assistant apparatus in accordance with seventh embodiment of the present invention is positioned. FIG. 13B is a partial cutaway perspective view of the assistant apparatus. FIG. 13C is a plan view showing a part of an elongated film.

Different points from the sixth embodiment are as follows:

(1) Through holes 25 are formed in not only the bottom plate but also the top plate of the bridging member 24.

(2) Not only openings 20 each covered by a diffusion limiting membrane 3, but also through holes 30 for allowing passing through of a concentration measuring electrode 28, are formed in a predetermined position on an elongated film 2'.

(3) A wetting liquid housing member 31 is secured to an under surface of a top plate of a test apparatus body 29a.

(4) An elevating mechanism (not shown) for elevating the concentration measuring electrode 28 up to the different heights, is provided at the predetermined position of the test apparatus body 29a.

(5) A switch (not shown) for starting measurement is provided at the predetermined position of the test apparatus body 29a.

(6) Not only holes 21, but also holes 21b for detecting the position of the through hole 30, are formed in the edge portion of the elongated film 2', each hole 21b has a predetermined relative relation the corresponding through hole 30.

The concentration measuring operations of blood sugar using the test apparatus with the assistant installed therein, are as follows.

Initially the cover 29 is opened after the test apparatus is ready for measuring which is caused by turning on the power switch (not shown), then blood drawn from a human body is deposited to the diffusion-limiting membrane 3 at the position opposite to the cover 29. While carrying out the series of operations above-mentioned, the concentration measuring electrode 28 is kept elevated through both through holes 25 and the through hole 30, and contacted with the wetting liquid housing member 31. Secondly, the concentration measuring electrode 28 is separated from the wetting liquid housing member 31 by turning on the switch for starting measurement, and lowered to the position not to interfere with the elongated film 2'. Thirdly, the elongated film 2' is moved for locating the diffusion-limiting membrane 3 with blood deposited thereon opposite to the concentration measuring electrode 28. Then the concentration measuring electrode 28 is elevated to be pressure contacted with the diffusion-limiting membrane 3. Fourthly, a value of blood sugar is detected and displayed based on the output signal of the concentration measuring electrode 28. After the detecting operation and displaying operation are carried out, the concentration measuring electrode 28 is lowered to be separated from the diffusion limiting membrane 3, then the elongated film 2' is moved by the predetermined distance for being placed opposite to the through hole 30 and the concentration measuring electrode 28. Finally the concentraion measuring electrode 28 is elevated through both through hole 25 and the through hole 30 to contact with the wetting liquid housing member 31, then the power switch is turned off to terminate the series of operations for measuring the value of blood sugar.

As is apparent from the foregoing, a state for measuring the value of blood sugar and a state for wetting the concentration measuring electrode 28 can easily be selected, although the assistant apparatus is kept positioned in the test apparatus body 29a. Manual operations are limited only to the turning on and off of the power switch, opening and closing of the cover 29, turning on and off of the switch for starting measurement, and the drawing blood operation and the depositing blood operation. As a result the series of measuring operations for measuring the value of blood sugar become very easy to carry out.

In a concrete example, the length of the elongated film 2' is 1200 mm, the diameter of the opening 20 and through hole 30 is 3 mm and 18 mm respectively, and the pitch between the neighboring holes (holes is a general term for the openings 20 and through holes 30) in 20 mm. The number of the openings 20 covered by the diffusion-limiting membrane 3 can be up to 30. As a result measurement of the value of blood sugar can be carried out for about two weeks without exchanging the assistance apparatus, based on the condition that measurement of the value of blood sugar is carried out twice per day.

In the embodiment above mentioned, the wetting liquid housing member 31 is secured to the top plate of the test apparatus body 29a, but the wetting liquid housing member 31 may be secured to the bridging member 21. If the latter configuration is employed, the wetting liquid housing member 31 is automatically exchanged with every change of the assistant apparatus. As a result, only a sponge and the like can be employed as the wetting liquid housing member 31.

Figure 14:
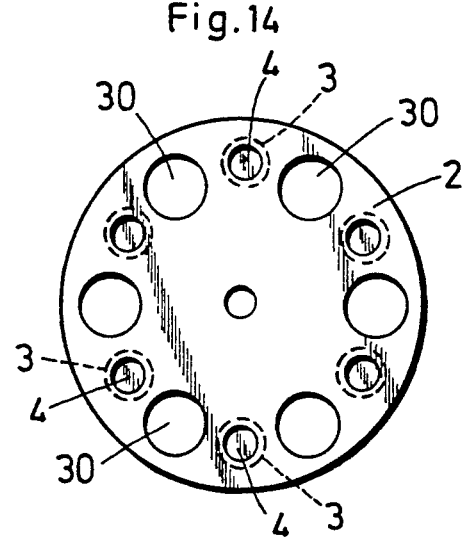
FIGS. 14 and 15B are plan views of a modified disk-shaped thin plate respectively.

Also in the embodiment above-mentioned, openings 20 and through holes 30 are formed reciprocally at the elongated film 2'. Another configuration shown in FIG. 14 may be employed. That is, openings 4 and through holes 30 are formed reciprocally at the disk-shaped thin plate 2 similar to the disk-shaped thin plate 2 in the first and second embodiments, and a disk-shaped thin plate driving mechanism (not shown) for rotating the disk-shaped thin plate 2 by a predetermined angle is provided with a test apparatus. This configuration operates similar to the embodiment shown in FIG. 13A.

Figure 15A:
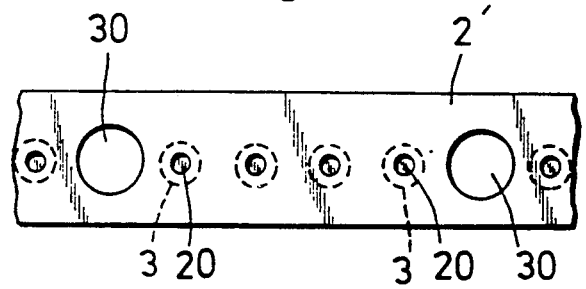
FIG. 15A is a plan view of a modified elongated film.
Figure 15B:
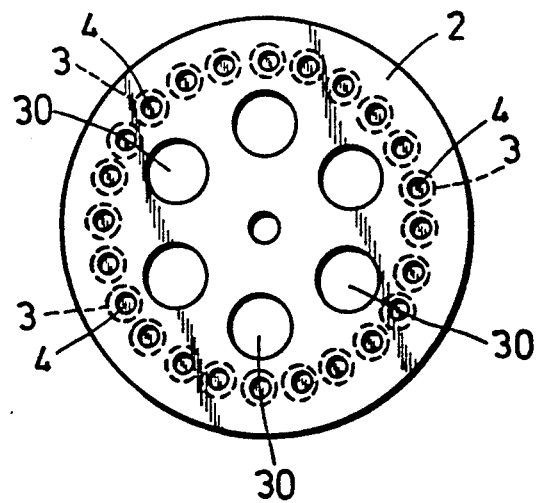

The other configuration is that through holes 30 are formed corresponding to every several openings 20 at the elongated film 2' as shown in FIG. 15A. A further configuration is that a plural number of openings 4 are formed in the edgeward portion of the disk-shaped thin plate 2 and a minority of through holes 30 are formed in the innerward portion of the disk-shaped thin plate as shown in FIG. 15B. Both configuration shown in FIGS. 15A and 15B permit an increase in the number of openings 4, 20 compared to the configurations shown in FIGS. 13C and 14. In these configurations, the elongated film 2' or disk-shaped thin plate 2 should be returned with every measurement of the value of blood sugar, and as a consequence the inner mechanism of the test apparatus becomes somewhat complex. But the number of possible measurements of the value of blood sugar by using one elongated film 2' or disk-shaped thin plate 2 is greatly increased, so the inconvenience of the inner mechanism being somewhat complex can be negligible.

In the foregoing embodiment, it is allowed that the concentration measuring electrode 28 is elevated to contact with the wetting liquid housing member 31 and the elongated film 2' or disk shaped thin plate 2 is lowered to contact the diffusion-limiting membrane 3 with the concentration measuring electrode 28, instead of elevating and lowering only the concentration measuring electrode 28 to selectively contact with the diffusion limiting membrane 3 or wetting liquid housing member 31.

FIG. 16A is a plan view of an elongated film.

Different points from the elongated film shown in FIGS. 11 and 13C are as follows:

(1) A plural number of openings 20 formed in the elongated film 2' are classified into two groups one after the other.

(2) The openings 20 belonging to one group are covered only by diffusion-limiting membranes 3.

(3) The openings 20 belonging to the other group are covered by diffusion-limiting membranes 3 and crushable calibrating standard solution housing member 32 in which standard solution for calibration having the established glucose concentration is housed.

Further, a crushing mechanism for crushing the calibrating standard solution housing member 32 is provided at a predetermined position of a test apparatus. The crushing mechanism may be a mechanism for applying pressing force to the calibrating standard solution housing member 32. Furthermore the crusing mechanism can easily be considered by a person having the ordinary skill in the art, so it is not shown in any drawing.

Measurement operation using the elongated film 2' above-mentioned is as follows.

Prior to the measurement of the value of blood sugar, measurement of the value of blood sugar is carried out based in the standard solution for calibration housed in the calibrating standard solution housing member 32, then changes with the passage of time of the test apparatus can be compensated for based on the obtained value. After that, an accurate value of blood sugar is obtained by measuring the concentration of blood sugar of the deposited blood.

As is apparent from the foregoing, the manual operation of dropping the standard solution for calibration onto the elongated film 2' can be omitted. Further the change of glucose concentration of the calibrating standard solution for calibration caused by germs and others, is securely prevented. As a result, extremely accurate measurement of the value of blood sugar is achieved with simplified manual operation.

FIG. 16B is a plan view of a disk-shaped thin plate.

A plural number of openings 4 are classified into two groups one after the other. The openings 4 belonging to one group are covered only by diffusion-limiting membranes 3, and the openings 4 belonging to the other group are covered by diffusion limiting membranes 3 and crushable calibrating standard solution housing member 32. So, the same function as the elongated film 2' shown in FIG. 16A is performed.

FIGS. 16C and 16D are plan views of an elongated film and a disk-shaped thin plate respectively.

A different aspect from the elongated film in Fig 16A and the disk-shaped thin plate in FIG. 16B is that the calibrating standard solution housing members 32 are secured to the elongated film 2' or disk-shaped thin plate 2 at every several openings 20 or 4. In these cases, the possible number of measurements of test solution is increased without increasing the number of openings 20 or 4.

Eighth Embodiment

Figure 17A:
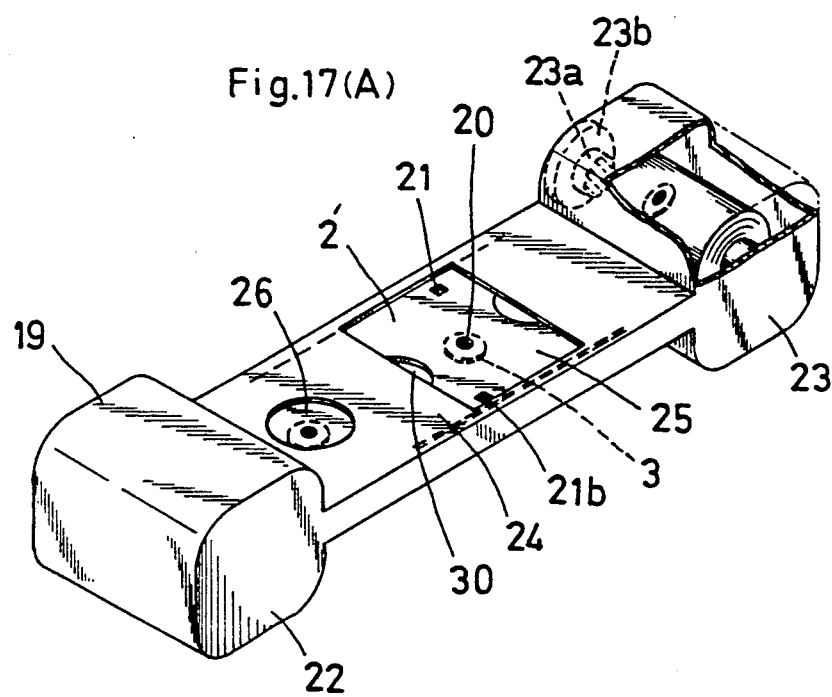
FIG. 17A is a partial cutaway perspective view of an assistant apparatus in accordance with an eighth embodiment of the present invention.

FIG. 17 is a partial cutaway perspective view of an assistant apparatus in accordance with an eighth embodiment of the present invention.

A different aspect from the seventh embodiment is that the opening 26 for depositing or dropping test solution is formed in the predetermined position of the bridging member 24 near the supplying chamber 22. Also the distance between adjacent opening 20 and through hole 30 is varied corresponding to the position of the opening 26.

Figure 17B:
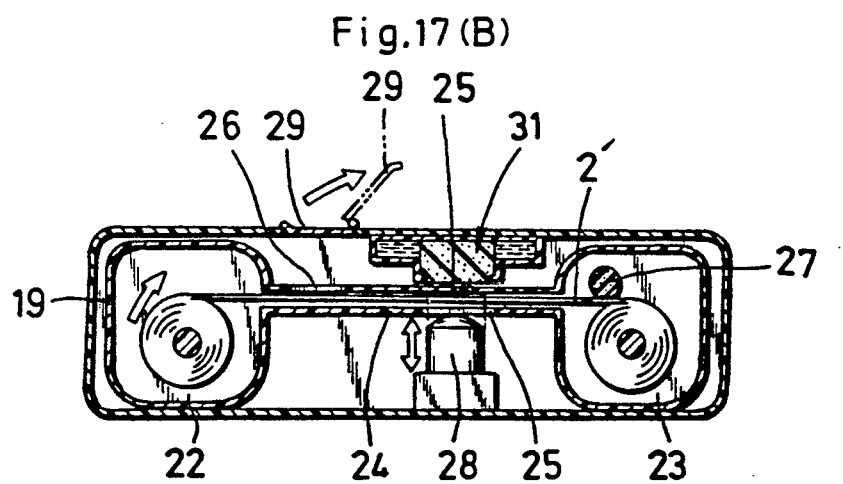
FIG. 17B is a simplified vertical section view of the center portion of a test apparatus in which the assistant apparatus in FIG. 17A is installed.

FIG. 17B is a schematic vertical section view at the center portion of a test apparatus having positioned therein the assistant apparatus.

A wetting liquid housing member 31 is secured to the test apparatus body 29a above the elongated film moving path opposite to a concentration measuring electrode 28. The opening 26 is positioned at the position being sufficiently separated horizontally from the wetting liquid housing member 31.

In this embodiment, test solution can easily be deposited or dropped to the elogated film 2' through the opening 26 without being interfered with by the wetting liquid housing member 31 After that the elongated film 2' is moved by the distance equal to the distance between the opening 26 and the through hole 25 for allowing insertion of the concentration measuring electrode 28, then the concentration measuring electrode 28 is elevated to contact with the diffusion-limiting membrane 3 thereby to measure the concentration of the test substance.

As is apparent from the foregoing, the distance between the through hole 30 and the following opening 20 is set to be large. So it seems that the number of openings 20 may be decreased. But the decrease of the number of openings 20 is prevented without lengthening the elongated film 2' by decreasing the distance between the through hole 30 and the prior opening 20.

Ninth Embodiment

Figure 18A:
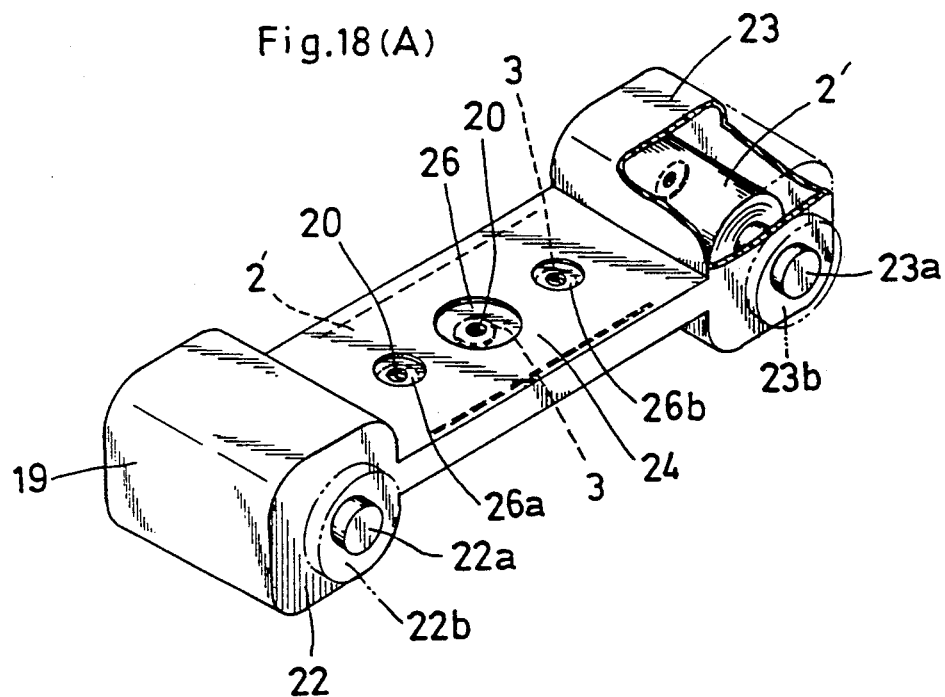
FIG. 18A is a partial cutaway perspective view of an assistant apparatus in accordance with a ninth embodiment of the present invention.

FIG. 18A is a partial cutaway perspective view of an assistant apparatus in accordance with a ninth embodiment of the present invention.

Different points from the seventh embodiment are as follows:

(1) A rotary shaft 22a provided with a supplying chamber 22 projects outwardly from a casing 19. A rotary engaging mechanism 22b engagable with a driving system provided with a test apparatus, is provided at the projected portion of the rotary shaft 22a.

(2) Not only an opening 26 for allowing deposition of test solution to an elongated film 2', but also openings 26a and 26b for dropping standard solution for calibration are formed in a bridging member 24 of the assistant apparatus. Both openings 26a and 26b are positioned symmetrically about the opening 26.

(3) Only openings 20 for allowing penetration of a test substance are formed in the elongated film 2', and no through holes 30 are formed at the elongated film 2'.

Figure 18B:
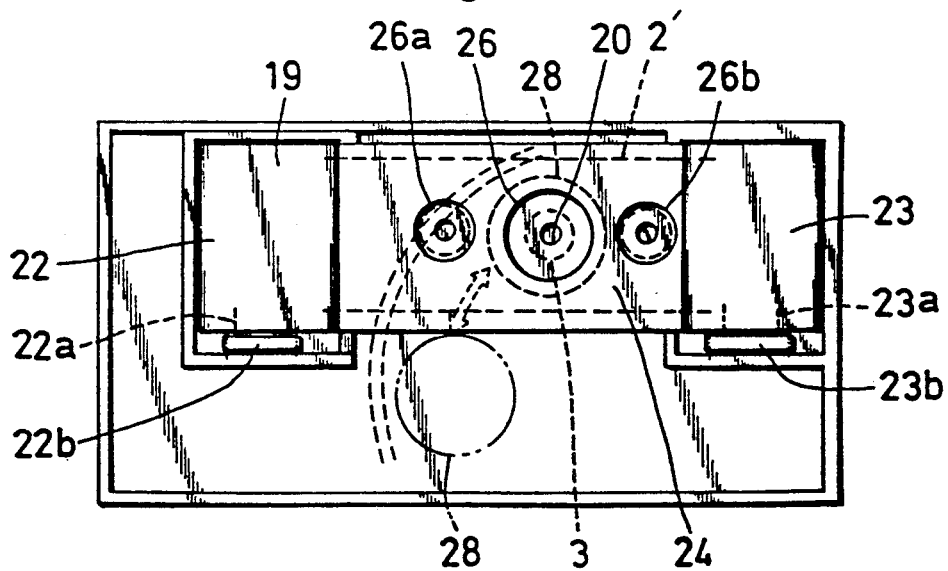
FIG. 18B is a simplified plan view of the center portion of a test apparatus in which the assistant apparatus in FIG. 17A is installed.

FIG. 18B is a schematic plan view of a test apparatus having the assistant apparatus positioned therein.

Openings 26a, 26 and 26b are formed in this order in the bridging member 24, and openings 20 for allowing penetration of test substance are exposed through the openings 26a, 26 and 26b. Further an electrode driving mechanism (not shown), for moving a concentration measuring electrode 28 along the horizontal plane and for moving the concentration measuring electrode 28 up and down at both positions horizontally moved to the limit, is provided with the test apparatus. One of the positions horizontally moved to the limit is the position opposite to the hole 20, while another is the position opposite to a wetting liquid housing member (not shown).

When measuring concentration only of a test solution is carried out, first the test solution is dropped to the opening 20 exposed through the opening 26. Secondly, the concentration measuring electrode 28 is moved downward to the maximum distance, then moved horizontally to one limit and further moved upward to contact with a diffusion-limiting membrane 3 covering the opening 20. Then the measurement of concentration is carried out. After that, first the concentration measuring electrode 28 is moved downward to the maximum distance, then moved horizontally to another limit and further moved upward to contact with the wetting liquid housing member. Secondly, winding power is transmitted to a rotary shaft 23a provided with the receiving chamber 23 through the rotary engaging mechanism 23b from the driving system, thereby to move the elongated film 2' toward the receiving chamber 23 by the distance equal to the distance between adjacent openings 20. Then the preparaion for next measurement is completed.

When the concentration of standard solution for calibration and the test solution in this order, first the standard solution for calibration is dropped onto the opening 20 exposed through the opening 26a, while the test solution is dropped onto the opening 20 exposed through the opening 26. Secondly, winding power is transmitted to the rotary shaft 23a through the rotary engaging mechanism 23b from the driving system, thereby to move the elongated film 2' toward the receiving chamber 23. Thirdly, the concentration measuring electrode 28 is moved downward to the maximum distance, then moved horizontally to one limit and further moved upward to contact with the diffusion-limiting membrane 3. Then the measurement of concentration the of standard solution for calibration is carried out. After that, first the concentration measuring electrode 28 is moved downward to the maximum distance, then moved horizontally to another limit and further moved upward to contact with the wetting liquid housing member. Instead of this movement, the concentration measuring electrode 28 may be moved only to its downward limit. Secondly, returning power is transmitted to the rotary shaft 22a through the rotary engaging mechanism 22b from the driving system, thereby to return the elongated film 2' toward the supplying chamber 22 by the distance equal to the distance between adjacent openings 20. Thirdly, the concentration measuring electrode 28 is moved to contact with the diffusion limiting membrane 3. Then the measurement of the concentration of the test solution is carried out. After that, first the concentration measuring electrode 28 is moved to contact with the wetting liquid housing member. Secondly, winding power is transmitted to the rotary shaft 23a through the rotary engaging mechanism 23b from the driving system, thereby to move the elongated film 2' toward the receiving chamber 23 by the distance equal to double the distance between adjacent openings 20. Then the preparation for next measurement is completed.

Further, at the initial stage after the assistant apparatus is installed in the test apparatus, winding power is transmitted to the rotary shaft 23a through the rotary engaging mechanism 23b from the driving system, thereby to move the elongated film 2' by the distance equal to the distance between adjacent openings 20.

Moving operations are not limited to those described above, but can be established as follows.

When measuring concentration of only the test solution is carried out, first the elongated film 2' is returned toward the suppling chamber 22 by the distance equal to the distance between adjacent openings 20, by transmitting returning force through the rotary engaging mechanism 22b accompanied by the closing of the cover. Secondly, the test solution is dropped to the opening 20 exposed through the opening 26. Thirdly, the concentration measuring electrode 28 is moved to contact with the diffusion limiting membrane 3 covering the opening 20. Then the concentration measurment is carried out. After that, first the concentration measuring electrode 28 is moved to contact with the wetting liquid housing member. Secondly, the elongated film 2' is moved toward the receiving chamber 23 by the distance equal to double the distance between adjacent openings 20, by transmitting the winding force through the rotary engaging mechanism 23b. Then the preparation for next measurement is completed.

When measuring concentration of standand solution for calibration and the test solution in this order, during the positioning of the elongated film 2' the cover of the test apparatus body is closed; afterwards it is kept open. In this state the standand solution for carlibration is dropped to the opening 20 exposed through the opening 26b which is formed in the downstream position from the opening 26 of the bridging member 24. Also the test solution is dropped to the opening 20 exposed through the opening 26. After that, first the elongated film 2' is returned toward the supplying chamber 22 by the distance equal to the distance between adjacent openings 20. Then the concentration measurement of the standand solution for carlibration is carried out. Subsequently the elongated film 2' is moved toward the receiving chamber 23 by the distance equal to the distance between adjacent openings 20. Then the concentration measurement of the test solution is carried out.

After both measurements are completed, first the concentration measuring electrode 28 is moved to contact with the wetting liquid housing member. Secondly, the elongated film 2' is moved toward the receiving chamber 23 by the distance equal to double the distance between adjacent openings 20. Then the preparation for next measurement is completed.

It is a matter of course that the apparatuses in accordance with the present invention may be applied to apparatuses for measuring a variety of liquids; e.g. cholesterol, neural fat, urine or the like and biological fluids.

Various modifications and applications may occur to those skilled in the art without departing from the spirit and scope of the invention as defined by the appended claims.

What is claimed is:

1. An assistant apparatus for measuring a concentration of a test substance in a liquid comprising:
    a thin plate having a plurality of openings through which a test substance to be measured is penetrated, and a diffusion limiting membrane covering each of said plurality of openings such that a separate diffusion limiting membrane covers each of said plurality of openings; or, alternatively, a plurality of thin plates, each thin plate having an opening through which a test substance to be measured is penetrated, and a diffusion limiting membrane covering said opening;

wherein the diffusion-limiting membrane limits diffusion of said test substance, a casing for housing said thin plate or plates, and a driving mechanism for moving said thin plate or plates by a predetermined distance, whereby said assistant apparatus is removably installed in a predetermined position of a test apparatus having a concentration measuring electrode therein such that the concentration measuring electrode can contact said diffusion limiting membrane covering one of said openings.

2. An assistant apparatus as set forth in claim 1, wherein the thin plate or plates is a single disk-shaped thin plate having a plurality of openings, the openings being spaced apart a predetermined distance at an edge portion of the thin plate, wherein the casing is further provided with an opening for dropping a test solution and a through hole for inserting the concentration measuring electrode, and wherein the driving mechanism further includes a rotary supporting member for rotatably supporting the thin plate.

3. An assistant apparatus as set forth in claim 2, wherein the plate further includes through holes for inserting the concentration measuring electrode located between adjacent openings.

4. An assistant apparatus as set forth in claim 3, wherein the openings and through holes are formed in the thin plate, one after the other.

5. An assistant apparatus as set forth in claim 3, wherein the through holes are formed in the thin plate after every predetermined number of openings.

6. An assistant apparatus as set forth in claim 2, wherein the thin plate further includes calibrating standard solution housing members for housing a standard solution for calibration, said standard solution having an established concentration of the test substance, wherein there is one calibrating standard solution housing member corresponding to every other opening.

7. An assistant apparatus as set forth in claim 2, wherein the thin plate includes calibrating standard solution housing members for housing a standard solution for calibration, said standard solution having an established concentration of the test substance, wherein there is one calibrating standard solution housing member corresponding to every predetermined number of openings.

8. An assistant apparatus as set forth in claim 1, wherein the thin plate or plates is a single elongated thin plate having a plurality of openings therein, the openings being formed at every predetermined distance in a center portion of the thin plate, wherein the casing has a supply chamber, a receiving chamber and a bridging member, said supplying chamber housing a part of said thin plate including one end thereof in a rolled state, said receiving chamber housing a part of said thin plate including another end thereof in a rolled state, said bridging member interconnecting said supplying chamber and said receiving chamber, and wherein the driving mechanism further includes a rotary shaft for winding said thin plate and a rotary engaging mechanism for transmitting a rotary force to said rotary shaft such that said thin plate is moved toward said receiving chamber.

9. An assistant apparatus as set forth in claim 8, wherein the bridging member is of a sufficient length for positioning two or more openings simultaneously.

10. An assistant apparatus as set forth in claim 9, wherein the bridging member further includes an opening for dropping test solution to the thin plate at a position in a direction toward the supplying-chamber.

11. An assistant apparatus as set forth in claim 9, further comprising:

a moving mechanism for moving the thin plate toward the supplying chamber, said moving mechanism including a rotary shaft for receiving said thin plate and a rotary engaging mechanism for transmitting a rotary force to said rotary shaft.

12. An assistant apparatus as set forth in claim 8, wherein the thin plate further includes through holes for passing the concentration measuring electrode between adjacent openings, and the bridging member further includes a through hole for passing said concentration measuring electrode therethrough.

13. An assistant apparatus as set forth in claim 12, wherein the openings and through holes are formed in the thin plate in an alternating manner.

14. An assistant apparatus as set forth in claim 12 wherein the through holes are formed in the thin plate after every predetermined number of openings.

15. An assistant apparatus as set forth in claim 8, wherein the thin plate further includes calibrating standard solution housing members for housing a standard solution for calibration, said standard solution having an established concentration of the test substance, wherein there is one calibrating standard solution housing member corresponding to every other opening.

16. An assistant apparatus as set forth in claim 8, wherein the thin plate further includes calibrating standard solution housing members for housing a standard solution for calibration, said standard solution having an established concentration of the test substance, wherein there is one calibration standard solution housing member corresponding to every predetermined number of openings.

17. An assistant apparatus for measuring a concentration of a test substance in a liquid comprising:

a plurality of thin plates, each having one opening through which a test substance to be measured is penetrated, a diffusion limiting membrane for limiting diffusion of said test substance adhered to each of said thin plates for covering said opening on the thin plates, such that each thin plate has one diffusion limiting membrane, a casing for housing said thin plates, and a driving mechanism for moving said thin plates by a predetermined distance, whereby said assistant apparatus is removably installed in a predetermined position of a test apparatus having a concentration measuring electrode therein such that the concentration measuring electrode can contact said diffusion limiting membrane, wherein the thin plates are strips, the opening on each plate being formed at a predetermined position on each thin plate, wherein the casing houses the thin plates therein in a piled up state, said casing further including an opening for sending out one strip of thin plate, and wherein the driving mechanism slides only one sheet of thin plate outwardly through the opening.

18. A test apparatus for measuring a concentration of a test substance in a liquid comprising:

an assistant apparatus having a thin plate with a plurality of openings through which a test substance to be measured is penetrated, and a diffusion limiting membrane covering each of said plurality of openings such that a separate diffusion limiting membrane covers each of said plurality of openings; or alternatively, said assistant apparatus having a plurality of thin plates, each thin plate having an opening through which a test substance to be measured is penetrated, and a diffusion limiting membrane covering said opening;

wherein the diffusion-limiting membrane limits diffusion of said test substance, a casing for housing said plate or plates;

a driving mechanism for moving said plate or plates, wherein said driving mechanism is provided at least partially with said casing;

a test apparatus body for positioning said assistant apparatus removably therein, and a concentration measuring electrode provided with said test apparatus body, whereby said assistant apparatus is positioned in said test apparatus body and said thin plate or plates are moved by said driving mechanism to a position where one of said diffusion-limiting membranes can contact said concentration measuring electrode.

* * * * *